US008440608B2

(12) United States Patent
Mane et al.

(10) Patent No.: US 8,440,608 B2
(45) Date of Patent: May 14, 2013

(54) BETA-SUBSTITUTED TETRANDROPYRANA (ON) S AND METHOD FOR THE SYNTHESIS AND THE USE THEREOF

(75) Inventors: Jean Mane, Grasse (FR); Jean-Jacques Chanot, Speracedes (FR); Martin Schroeder, Kent (GB)

(73) Assignee: V. Mane Fils, Bar sur Loup (FR)

( * ) Notice: Subject to any disclaimer, the term of this patent is extended or adjusted under 35 U.S.C. 154(b) by 1175 days.

(21) Appl. No.: 11/659,501

(22) PCT Filed: Aug. 5, 2005

(86) PCT No.: PCT/FR2005/002038
§ 371 (c)(1),
(2), (4) Date: Feb. 6, 2007

(87) PCT Pub. No.: WO2006/021663
PCT Pub. Date: Mar. 2, 2006

(65) Prior Publication Data
US 2008/0032914 A1    Feb. 7, 2008

(30) Foreign Application Priority Data

Aug. 6, 2004   (FR) ..................... 04 08729

(51) Int. Cl.
*A61K 8/18*      (2006.01)
*A61Q 13/00*     (2006.01)
*C07D 321/00*    (2006.01)
*C07D 305/00*    (2006.01)
*C07D 407/00*    (2006.01)
*C07D 493/00*    (2006.01)

(52) U.S. Cl.
USPC .................. 512/11; 512/1; 512/25; 549/200; 549/263; 549/356

(58) Field of Classification Search ..................... 512/25, 512/1, 11; 549/200, 263, 356
See application file for complete search history.

(56) References Cited

U.S. PATENT DOCUMENTS

| 3,248,327 | A | * | 4/1966 | Whitaker | 508/307 |
| 3,527,770 | A | * | 9/1970 | Stapp | 549/356 |
| 4,288,350 | A | | 9/1981 | Nieuwland et al. | |
| 5,124,417 | A | * | 6/1992 | Farooq | 526/90 |
| 5,510,326 | A | * | 4/1996 | Noire | 512/11 |
| 5,665,696 | A | * | 9/1997 | Noire | 512/11 |
| 2002/0035055 | A1 | * | 3/2002 | Gautschi et al. | 512/20 |

FOREIGN PATENT DOCUMENTS

| DE | 103 53 656 | 6/2004 |
| DE | 103 53 658 | 6/2004 |

OTHER PUBLICATIONS

Anselmi et al. J. Agric. Food Chem. 1994 vol. 42 pp. 2876-2879.*
Anselmi et al. (J. Agric. Food Chem. 1994 vol. 42 pp. 2876-2879).*
Kayser et al. (Journal of Organic Chemistry, 1998 vol. 63 pp. 7103-7106).*
Evans, David A., "C2-Symmetric Cu(II) Complexes as Chiral Lewis Acids. Catalytic Enantioselective Michael Addition of Silylketene Acetals to Alkylidene Malonates", Journal of American Chemistry Society, 1999, vol. 121, pp. 1994-1995.
Stapp, Paul R, "The Reaction of α Olefins with Paraformaldehyde and Hydrogen Halides. A Novel Tetrahydropyran Synthesis", The Journal of Organic Chemistry, vol. 34, No. 3, Mar. 1969.
Montaudon et al., "No. 516.—Additions radicalaires. XII.—Addition d'heterocycles oxygenes aux acetyleniques vrais", Bull. Soc. Chim. Fr., 1974, vol. 11, pp. 2635-2638.
Montaudon et al., "Synthese de nouveaux alkyl-2 et -3 tetrahydrofurannes et -pyrannes", J. Heterocycl. Chem., 1979, vol. 16, No. 11, pp. 113-121.
Hiratake et al., "Highly Regioselective Ring-Opening of α Substituted Cyclic Acid Anhydrides Catalyzed by Lipase", Tetrahedron Letters, vol. 30, No. 12, pp. 1555-1556, 1989.
Gansauer et al., "Emergence of a Novel Catalytic Radical Reaction: Titanocene-Catalyzed Reductive Opening of Epoxides", Journal of American Chemistry Society, 1998, vol. 120, pp. 12849-12859.
Corbin et al., "Stereochemical Assignments of the 7-Phenyl-3-Oxabicyclo [4.1.0] Heptanes", Journal of Heterocyclic Chemistry, vol. 18 No. 3, pp. 643-644, 1981, XP001205571.
Woodyard et al., "The Synthesis of the Benzyltetrahydropyrans", Journal of Heterocyclic Chemistry, vol. 13, No. 3, Jun. 1976, pp. 647-648; XP001205569.
Gevorkyan, et al. "Cycloalkylation of Acetylenic and Allenic Hydrocarbons With Bis(Halomethyl) Ethers. New Synthesis of Pyran Derivatives", Dokl. Vses. Konf. Khim. Atsetilena. 4th, vol. 1, pp. 152-157, 1973, XP009045120.
Metzger et al., "AluminumChloride-Induced Additions of Formaldehyde to Alkenes", Bulletin Des Societes Chim. Belg., vol. 103 Nos. 7-8, pp. 393-397, XP009045126, 1994.
Volynskii et al., "Preparative Synthesis of 3-Alkyl(Cycloalkyl)Thiacyclohexanes", Izvestiya Akademii Nauk Sssr, Seriya Khimicheskaya, 1976, vol. 10, pp. 2299-2302, XP009045115. Peng et al., "Compositions of Volatile Oil of Primula obconica in Central China", Natural Product Letters, vol. 16, No. 4, pp. 248-253, XP000945122, 2002.
Butler, George B., "Radical Cyclo- and Cyclocopolymerization", Journal of Polymer Science: Polymer Symposium, vol. 64, pp. 71-93, XP009045116, 1978.
Hartung et al., Towards Improved Alkoxyl Radical Precursors—The Synthesis of N-Alkoxy-4-(p-Chlorophenyl) Thiazole-2(3h)-Thiones, pp. 848-850, XP001205572, SYNLET (Letters) Jul. 1997.
Kayser et al., "Enantio- and Regioselective Baeyer-Villiger Oxidations of 2- and 3- Substituted Cyclopentanones Using Engineered Bakers' Yeast", Journal of Organic Chemistry, vol. 63, pp. 7103-7006, XP001205391, 1998.
Crich et al., "Generation and Trapping of Alkene Radical Cations Under Nonoxidizing Conditions: Formation of Six-Membered Rings by Exo- and Endo-Mode Cyclizations", Organic Letters, 2002, vol. 4, No. 15, pp. 2573-2575, XP001205566.

(Continued)

*Primary Examiner* — Patrick Ryan
*Assistant Examiner* — Aaron Greso
(74) *Attorney, Agent, or Firm* — Young & Thompson

(57) ABSTRACT

The invention relates, in particular to a tetrahydropyran(on) compound which is substituted in position beta with respect to a cycle oxygen of formula (I), wherein a substituent R is a linear alkyl radical in C2:C10 including, $(CH_3)_2CH-$ or $C_6H_5-(CH_2)_m-$, with m=0 or 1, or formula (II), wherein A is $-CH_2-$ or $-CO-$, in the form of an odorant and to a method for the synthesis thereof by reducing oxo-ester. The use of the inventive compound in composition such as perfumery compositions in the ordinary sense of the term i.e. topic, in particular cosmetic compositions and care products.

15 Claims, No Drawings

OTHER PUBLICATIONS

Lemoult et al., "Lipase-Catalyzed Baeyer-Villiger Reactions" Journal of the Chemical Society Perkins Transactions, vol. 2, 1995, pp. 89-91, XP002928285.

Yamaguchi et al., "A New Synthesis of Delta-Lactones from Oxetanes", Tetrahedron Letters, vol. 25, No. 11, pp. 1159-1162, XP001205395, 1984.

Wang et al., "Access to Optically Pure 4- and 5-Substituted Lactones: a Case of Chemical-Biocatalytical Cooperation", Journal of Organic Chemistry, vol. 68, No. 16, 2003, pp. 6222-6622.

* cited by examiner

BETA-SUBSTITUTED TETRANDROPYRANA(ON) S AND METHOD FOR THE SYNTHESIS AND THE USE THEREOF

The present invention relates in general to the field of fragrant agents and to the use thereof especially in perfumery, in particular in topical compositions and maintenance products. In particular, the present invention relates to the use, as fragrant agents, of tetrahydropyran(one) compounds—i.e. tetrahydropyrans and tetrahydropyranones—substituted in the beta position relative to the ring oxygen, as a result of their citrus, verbena, fruity or nitrile notes, and also relates to the process for synthesizing them.

The term perfumery is used herein to denote not only perfumery in the usual sense of the term, but also other fields in which the odor of products is important. These may be perfumery compositions in the usual sense of the term, such as fragrancing bases and concentrates, eaux de Cologne, eaux de toilette, fragrances and similar products; topical compositions—in particular cosmetic compositions—such as facial and body creams, talc powders, hair oils, shampoos, hair lotions, bath salts and oils, shower and bath gels, toiletry soaps, antiperspirants and body deodorants, shaving lotions and creams, soaps, creams, toothpastes, mouthwashes, salves and similar products; and maintenance products, such as softeners, detergents, laundry washing products, ambient deodorizers, and similar products.

The term "fragrant" is used herein to denote a compound that gives off an odor.

Certain lactones (i.e. tetrahydropyranones) and certain pyrans are already used in perfumery. Most of the lactones used in perfumery are fatty acid derivatives and are thus substituted in position 6, for instance γ-decalactone or γ-dodecalactone which give a fruity, balsamic note to fragrant compositions. This is likewise the case for the use of pyrans in perfumery, which are also substituted in the alpha position relative to the oxygen incorporated in the ring. To mention but two: rose oxide and Doremox® from Firmenich give typical notes for rose compositions.

There is a need for other fragrant agents in order to broaden the range of notes that may be given to a composition and the options available for adding these notes.

Moreover, the known synthetic processes may be improved. Tetrahydropyranones have often been synthesized via enzymatic oxidation of the corresponding ketone as described by Margaret M. Kayser et al., *Journal of Organic Chemistry* (1998), 63 (20), 7103-7106; and Stephanie C. Lemoult et al., *Journal of the Chemical Society, Perkin Transactions 1: Organic and Bio-Organic Chemistry* (1995), (2), 89-91. Chemically, they are synthesized from oxetanes (Masahiko Yamaguchi et al., *Tetrahedron Letters* (1984), 25 (11), 1159-62) or via a Mukaiyama-Michael reaction between silylketene acetals and alkylidenemalonates (David A. Evans et al., *J. Am. Chem. Soc.* (1999), 121 (9), 1994-1995).

Four main synthetic routes have been used for the synthesis of tetrahydropyrans: the Prins reaction, as already described by Paul R. Straps in *J. Org. Chem*; (1969), 34 (3), 479-85, the radical addition of acetylene derivatives to tetrahydropyran (Montaudon, E. et al., *Bull. Soc. Chim. Fr.* (1974), 11, Pt. 2, 2635-8) or via cyclization of a diol, synthesized from a diacid, as described by E. Montaudon et al., (*J. Heterocycl. Chem.* (1979), 16 (11), 113-21) and Paul R. Strapp in the abovementioned publication.

However, these processes are difficult to perform on an industrial scale. It is thus necessary to find a synthetic route that can be industrialized while at the same time giving access to a large number of different compounds.

One subject of the invention is a fragrant agent consisting of a tetrahydropyran(one) compound substituted in the beta position relative to the ring oxygen, represented by the following formula:

(I)

in which the substituent R represents a linear alkyl radical $CH_3-(CH_2)_n-$ with n=2 to 10 inclusive, $(CH_3)_2CH-$ or $C_6H_5-(CH_2)_m-$, with m=0 or 1;

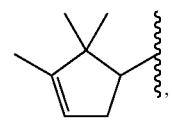

and in which A represents $-CH_2-$ or $-CO-$.

More specifically, a subject of the invention is a fragrant agent consisting of a tetrahydro-2H-pyran-2-one or tetrahydropyran compound, substituted in the beta position relative to the ring oxygen, of formulae (Ia) and (Ib), respectively:

(Ia)

(Ib)

in which R has the same meaning as in formula (I). Formula (Ia) corresponds to formula (I) in which A represents $-CO-$.

Formula (Ib) corresponds to formula (I) in which A represents $-CH_2-$.

In other words, a subject of the invention is the use, as a fragrant agent, of a compound of formula (I), (Ia) or (Ib).

In certain embodiments, R represents in formula (I), (Ia) or (Ib) a linear alkyl radical $CH_3-(CH_2)_n-$ with n=4 to 10 inclusive. In certain embodiments, R represents in this formula a linear alkyl radical $CH_3-(CH_2)_n-$ with n=4 to 8 inclusive, or alternatively a linear alkyl radical $CH_3-(CH_2)_n-$ with n=6 to 10 inclusive.

In particular, a subject of the invention is a fragrant agent chosen from the following fragrant agents, in other words the use as a fragrant agent of one of the following molecules:
5-pentyltetrahydropyran-2-one,
3-heptyltetrahydropyran,
5-heptyltetrahydropyran-2-one,
3-benzyltetrahydropyran,
the substituents corresponding to R in formula (I) being linear.

Among the fragrant agents represented in formula (I), some are, to the inventors' knowledge, novel molecules which are thus claimed as such. They are:

5-pentyltetrahydropyran-2-one,
5-nonyltetrahydropyran-2-one,
5-benzyltetrahydropyran-2-one,
5-(2,2,3-trimethylcyclopent-3-enyl)tetrahydropyran-2-one,
3-heptyltetrahydropyran,
3-octyltetrahydropyran,
3-nonyltetrahydropyran,
3-decyltetrahydropyran,
3-undecyltetrahydropyran, and
3-(2,2,3-trimethylcyclopent-3-enyl)tetrahydropyran,
the substituents corresponding to R in formula (I) being linear.

In other words, a subject of the invention is molecules of formula (I)

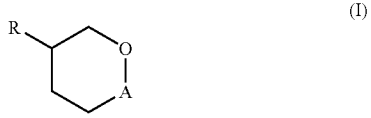

in which
the substituent R represents a linear alkyl radical $CH_3-(CH_2)_n-$ with n=6 to 10 inclusive,

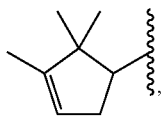 [SMILES: *C1CC=C(C)C1(C)C]

when A represents $-CH_2-$,
and
the substituent R represents a linear alkyl radical $CH_3-(CH_2)_n-$ with n=4, 6 or 8, or $C_6H_5-$

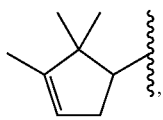 [SMILES: *C1CC=C(C)C1(C)C]

when A represents $-CO-$.

To the inventors' knowledge, none of the compounds represented in formula I has to date been described as having fragrant properties, and none has to date been used in perfumery.

A subject of the invention is also a composition comprising a base product and an effective amount of a compound of formula (I) as defined above.

It may be a fragrancing composition in which the fragrant agent is used to mask or neutralize certain odors, or alternatively to significantly improve the olfactive note of this same composition. Specifically, the fragrant agent of formula (I) gives the fragrancing composition that comprises it a richer, more dynamic, more intense and broader olfactive note than the same fragrancing composition without its presence. Said composition may be chosen from perfumery compositions in the usual sense of the term, such as fragrancing bases and concentrates, eaux de Cologne, eaux de toilette, fragrances and similar products; topical compositions—in particular cosmetic compositions—such as facial and body creams, talc powders, hair oils, shampoos, hair lotions, bath salts and oils, shower and bath gels, toiletry soaps, antiperspirants and body deodorants, shaving lotions and creams, soaps, creams, toothpastes, mouthwashes, salves, and similar products; and maintenance products, such as softeners, detergents, laundry washing products, ambient deodorizers, and similar products.

The base product will be readily-determined by a person skilled in the art as a function of the intended composition and thus of the intended use, for which the usual components—such as solvent(s) and/or adjuvants(s) as nonlimiting examples—are well known.

The effective amount of the compound of formula (I) incorporated into the composition will vary according to the compound, the nature of the composition, the desired fragrant effect, and the nature of the other fragrant or non-fragrant compounds that may be present, and may be readily determined by a person skilled in the art, given that it may vary within a very wide range, from 0.1% to 99% by weight, in particular 0.1% to 50% by weight and especially 0.1% to 30% by weight.

A compound of formula (I) may be present in the form of an isomer or a mixture of isomers, in particular an enantiomer or a mixture of enantiomers, or a racemic mixture.

Said compound may be used as sole fragrant agent or, as is common in perfumery, it may be in a mixture with one or more other fragrant compounds, that a person skilled in the art is capable of selecting as a function of the desired effect. The additional fragrant agent(s) may be compounds of formula (I) or other fragrant agents known to those skilled in the art.

Said compound may be used as such or it may be incorporated into or onto an inert support material or a material that may contain other active ingredients of the finished composition. A wide variety of support materials may be used, including, for example, polar solvents, oils, greases, finely divided solids, cyclodextrins, maltodextrins, gums, resins and any other support material known for such compositions.

A subject of the invention is also a process for synthesizing compounds of formula (I). A synthetic scheme relative to one embodiment is presented below.

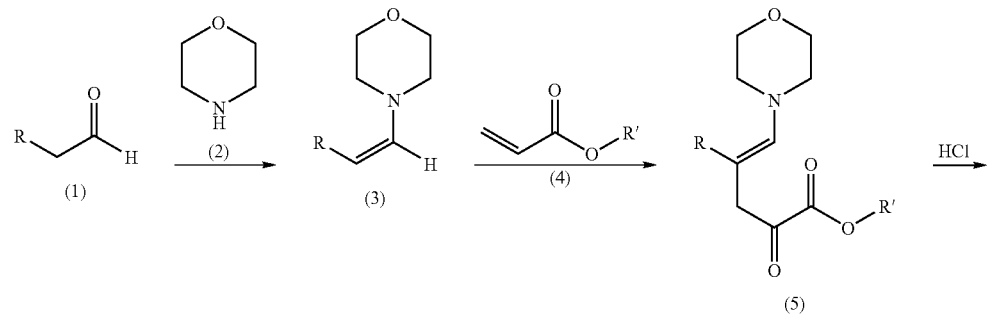

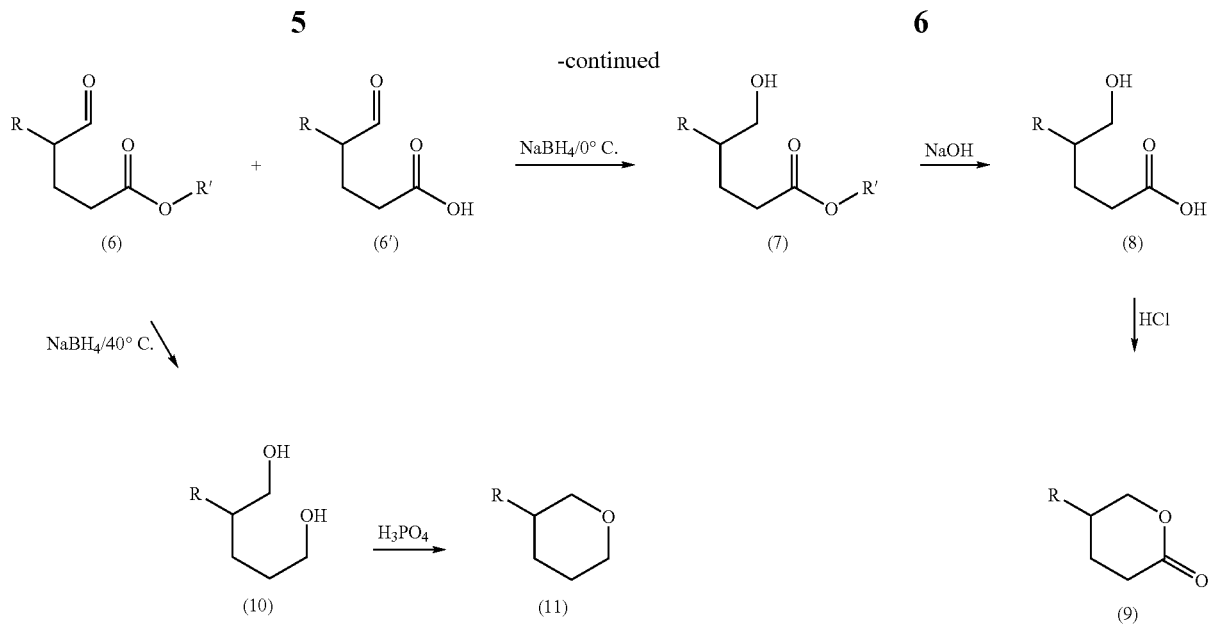

in which R has the same meaning as in formula (I), (Ia) or (Ib), and R' represents $CH_3$ or $C_2H_5$ or a higher alcohol ester, preferably a commercially available product such as $CH_3$ or $C_2H_5$ so as not to increase the cost of the synthesis.

In this scheme, compound (9) corresponds to a compound of formula (Ia), whereas compound (11) corresponds to a compound of formula (Ib).

All the compounds of formula (I) may be synthesized by reduction starting with a single oxo ester compound of formula (6)

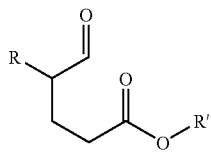

in which R has the same meaning as in formula (I) and R' represents $CH_3$ or $C_2H_5$— or a higher alcohol ester.

A subject of the invention is thus a process for synthesizing a compound of formula (I), comprising the reduction of an oxo ester compound of formula (6).

Depending on the reduction reaction conditions, a compound of formula (Ia) or (Ib) is obtained.

The oxo ester compound (6) may be synthesized via a process comprising the condensation of a secondary amine with an aldehyde, to form an enamine, followed by condensation of the enamine obtained with an acrylate, to form an enamine ester which is hydrolyzed to an oxo ester. This synthetic route has the advantage of limiting the self-condensation reactions of the aldehyde.

In one preferred embodiment of the invention, the oxo ester compound (6) is synthesized in the following manner.

In a first stage, an enamine (3) is formed from an aldehyde (1) and a secondary amine. This reaction is preferably performed with a cyclic amine, for instance piperidine or morpholine (2), but other amines, such as acyclic amines, may also be used. Morpholine is advantageous for economic reasons (low cost). The reaction does not require the use of a catalyst, but catalysts usually used for the formation of enamines may be used. Their use does not increase either the yield or the degree of conversion; however, they may increase the rate of the reaction. The secondary amine (2) is heated in a solvent, for instance cyclohexane, to the temperature at which the azeotrope of the solvent and of water begins to distill. The aldehyde (1) is added at this temperature, preferably slowly so as to minimize its self-condensation. At the end of the reaction, the solvent and the excess secondary amine (2) are evaporated off under reduced pressure. The enamine (3) (which is an alkenylmorpholine when the secondary amine is a morpholine) is used directly in the following reaction. A purification by distillation is not necessary and does not increase the yield of the subsequent Michael reaction.

A suitable base such as potassium hydroxide in methanol (about 1 mol %) is added to the enamine (3), and the mixture is preferably brought to about 50° C. An acrylate (4) is added slowly and the reaction medium is again stirred, preferably at a high temperature, after the end of the addition. An enamine ester (5) is thus formed. If the reaction is performed at a lower temperature, the conversion is slow, whereas a higher temperature (of about 50° C.) promotes the polymerization of the acrylate (4) and is thus preferred.

The enamine ester (5) is then hydrolyzed with a suitable acid, to give the oxo ester (6). Hydrolysis is performed at a temperature of about 20° C. to 80° C., preferably about 60° C. The appropriate acid used in the hydrolysis of the enamine ester (5) may be a mineral acid, for instance hydrochloric acid or sulfuric acid, or alternatively a solution of acetic acid buffered with sodium acetate. Treatment with acetic acid has the advantage of being milder and gives a higher yield for the oxo ester (6) than a treatment with hydrochloric acid, for example. Under the conditions described above, the partial saponification of the oxo ester (6) to the corresponding oxo acid (6') cannot be entirely avoided. The duration of the hydrolysis should thus be carefully chosen so as to limit the formation of the corresponding oxo acid (6'). In particular, this duration is from 2 hours to 8 hours and preferably 3 hours to 6 hours. The reaction yield is about 60-70%.

A subject of the invention is a process for synthesizing a compound of formula (I), the process comprising the reduction of an oxo ester of formula (6)

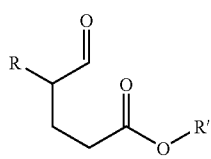

(6)

in which R has the same meaning as in formula (I) and R' represents CH₃ or C₂H₅— or a higher alcohol ester.

According to the conditions of reduction of the oxo ester (6), either a hydroxy ester (7) is obtained, which is a precursor of a lactone derivative (9), corresponding to a compound of formula (Ia), or a diol (10) is obtained, which leads, via acid treatment, to a pyran (11) corresponding to a compound of formula (Ib).

The hydroxy ester (7) is not isolated: it is converted to a lactone in a yield of 60-70%, generally 67%.

The diols are isolated and converted to the corresponding tetrahydropyrans in yields of about 60-70%.

The overall yield for the synthesis according to the invention is about 35-45%, both for the production of the products of formula (Ia) and of the products of formula (Ib).

A subject of the invention is a process for synthesizing a compound of formula (I), the process comprising the reduction of an oxo ester of formula (6) with a suitable reducing agent,
  a) at low temperature, to form a hydroxy ester (7), followed by saponification with a suitable base, and then hydrolysis with a suitable acid, followed by cyclization to form a compound of formula (Ia), or
  b) at high temperature, to form a diol (10), followed by cyclization to form a compound of formula (Ib).

The term "low temperature" means a temperature from about −10° C. to 10° C., preferably from about −5° C. to 5° C. and more preferably of about 0° C. The term "high temperature" means a temperature from about 30° C. to 50° C., preferably from about 30° C. to 40° C. and more preferably of about 35° C.

Needless to say, a person skilled in the art will appreciate that the amount of reducing agent required is variable depending on whether only the aldehyde is reduced or whether the two functions are reduced, and he will be able to determine the appropriate amount as a function of the intended objective. As a guide, for the reduction of the aldehyde, it is appropriate to add about 0.25 equivalent (mol) and about 0.75 equivalent (mol) for the reduction of the two functions.

A suitable reducing agent for the selective reduction of the aldehyde function may be sodium borohydride or polymethylhydrosiloxanes or boranes. Strong reducing agents are required for the formation of the diol, for example sodium borohydride, lithium aluminum hydride, aluminum triisopropoxide or simply sodium.

In one embodiment of the process according to the invention, the reduction of the oxo ester (6) using a reducing agent, for example sodium borohydride or polymethylhydrosiloxane, may be performed at low temperature, i.e. from about −10° C. to 10° C., preferably from about −5° C. to 5° C. and more preferably at about 0° C., in a suitable solvent such as ethanol or methanol, with an amount of reducing agent corresponding to about 0.2 to 0.3 molar equivalent and preferably slightly more than about 0.25 molar equivalent (optionally increased by the amount required to neutralize the oxo acid (6') present in the reaction medium if the oxo ester has been synthesized via the process described above). A hydroxy ester (7) is thus obtained. The hydroxy ester may be saponified directly, without the need for recovery, with a suitable base such as sodium hydroxide in aqueous medium. The aqueous phase is then extracted with a suitable solvent such as toluene to remove the alcohol that forms from the aldehyde of self-condensation of the starting aldehyde. The reaction medium is then acidified with a suitable acid such as hydrochloric acid, which allows simultaneous hydrolysis of the boron salts and the sodium salts of the hydroxy acid (8). The hydroxy acid (8) cannot be isolated since it cyclizes spontaneously in acidic medium, forming a δ-lactone (9) corresponding to a compound of formula (Ia). The lactone is recovered and purified by distillation.

In another embodiment of the process according to the invention, the reduction of the oxo ester by means of a reducing agent, for example sodium borohydride or lithium aluminum hydride, is performed at a temperature of about 30° C. to 50° C., preferably of about 30° C. to 40° C. and more preferably about 35° C., in a suitable solvent such as ethanol or isopropanol, with an amount of reducing agent corresponding to about 0.6 to 1.2 molar equivalents and preferably slightly more than one molar equivalent (optionally supplemented with the amount necessary to neutralize the oxo acid (6') present in the reaction medium if the oxo ester was synthesized via the process described above). The ester function is reduced to give a diol (10). The reaction medium is then acidified with a suitable acid, such as hydrochloric acid, and the aqueous medium is extracted with a suitable solvent such as toluene to recover the diol. A diol of low molecular mass, in particular, is highly soluble in water. Care should thus be taken to ensure that the recovery of the diol (10) is quantitative. The diol (10) is then purified by distillation, followed by cyclization, for example by treating the diol with a suitable acid such as 85% phosphoric acid, at a suitable temperature, in particular between 120° C. and 140° C., to form a pyran (11) corresponding to a compound of formula (Ib). The pyran (11) is recovered and purified by distillation.

The processes for synthesizing a compound of formula (I) comprising the reduction of an oxo ester of formula (6) may include the steps of synthesizing the oxo ester of formula (6) described above in combination with the processes for synthesizing said oxo ester.

The examples that follow further illustrate the fragrant agents according to the invention, and also the use, synthesis and value thereof. These examples are given merely for the purpose of illustration and cannot be considered as limiting the scope of the invention.

EXAMPLE 1

Synthesis of methyl 4-formylnonanoate (6)

418.0 g (4.80 mol) of morpholine and 344.0 g of cyclohexane are placed in a four-liter round-bottomed flask with a magnetic stirrer, a water separator, a thermometer and an addition funnel. The mixture is brought to a temperature of 65° C. to 70° C. 444.2 g (3.89 mol) of heptanal are added over five hours. The boiling point (80° C.-84° C. at the start of addition and then 87° C. toward the end of the operation) is thus rapidly obtained. The water formed during the reaction is recovered in a water separator. The reaction medium is then cooled and the cyclohexane and the excess morpholine are distilled off under reduced pressure (about 4400 Pa) without exceeding 80° C. in the bulk. The mixture is cooled to 40° C., brought to ambient pressure and 4.0 g of potassium hydroxide in 40 ml of methanol are added to the 4-hept-1(E/Z)-enylmorpholine. The mixture is brought to 60° C. and 237.5 g (2.76 mol) of methyl acrylate are then added over 4 hours. The mixture is stirred for 12 hours at 60° C. and a further 165.3 g (1.92 mol) of methyl acrylate are then added over two hours thirty minutes. At the end of the addition, the temperature of the reaction medium is increased to 80° C. and stirring is continued for 12 hours. An aqueous solution of acetic acid buffered to pH 4 (587.3 g of acetic acid, 215.3 g of sodium acetate trihydrate and 697.5 g of water) is added dropwise over two hours at this temperature. Stirring is continued for a further four hours. The phases are allowed to settle and are separated. The aqueous phase is extracted twice with 200 ml of cyclohexane. The organic phases are combined and washed once with 100 ml of water, once with 100 ml of saturated sodium bicarbonate solution and once with 150 ml of brine. The resulting organic phase is dried over magnesium sulfate. After evaporating off the solvent under reduced pressure (3990 Pa), without exceeding 50° C. in the bulk, 890.0 g of crude oxo ester are obtained, and are blanched under high vacuum (80° C. to 95° C. at 80 Pa) to give 663.0 g of 82.7% methyl 4-formylnonanoate (yield: 2.74 mol; 70%).

EXAMPLE 2

Synthesis of 5-pentyltetrahydropyran-2-one (9)

1560.0 g of ethanol and 663.0 g (max. 2.74 mol) of 82.7% methyl 4-formylnonanoate obtained in Example 1 are placed in a four-liter round-bottomed flask with a mechanical stirrer and a thermometer, and the mixture is cooled to 0° C. 41.6 g (1.10 mol) of sodium borohydride are then added dropwise over four hours, without exceeding 5° C. in the bulk. Stirring is continued after the end of the addition for a further 24 hours at 0° C. 1900.0 g of aqueous 10% sodium hydroxide solution are added dropwise over two hours, without exceeding 10° C. in the bulk. A white precipitate forms. Stirring is continued until the dissolution of the precipitate is complete (about two hours). The flask is placed under a vacuum of about 3990 Pa and the ethanol is distilled off. The aqueous phase obtained is extracted twice with 200 ml of a mixture of toluene and hexane (50/50) to remove the neutral products. The aqueous phase is then cooled to 0° C. The resulting phase is acidified with 1900.0 g of 10% hydrochloric acid for three hours, without exceeding 10° C. in the bulk. After the end of the addition, stirring is continued for four hours, while allowing the temperature of the reaction medium to rise to room temperature (20° C.). The phases are allowed to separate by settling and the organic phase is recovered. The aqueous phase is extracted twice with 200 ml of toluene. The organic phases are combined and are washed twice with 100 ml of water and once with 200 ml of brine, and then concentrated under reduced pressure (3990 Pa). 696.0 g of a crude product are obtained, and are then blanched at 133 Pa to give 468.0 g of 86.1% 5-pentyltetrahydropyran-2-one. After distillation on a Vigreux column, a core fraction of 289.0 g (1.70 mol) of 98.3% 5-pentyltetrahydropyran-2-one is obtained (90-2° C./27 Pa) in a yield of 61%.

EXAMPLE 3

Synthesis of methyl 4-formylundecanoate (6)

104.4 g (1.20 mol) of morpholine and 210.0 g of cyclohexane are placed in a one-liter round-bottomed flask with a magnetic stirrer, a water separator, a thermometer and an addition funnel. The mixture is brought to a temperature of 65° C. to 70° C. 142.0 g (0.99 mol) of nonanal are added over four hours. The boiling point (80° C.-84° C. at the start of the addition and then 87° C. toward the end of the operation) is thus rapidly obtained. The water formed during the reaction is recovered in a water separator. The reaction medium is then cooled and the cyclohexane and the excess morpholine are distilled off under reduced pressure (about 4400 Pa), without exceeding 60° C. in the bulk. The mixture is cooled to 40° C. and returned to ambient pressure, and 1.5 g of potassium hydroxide in 20 ml of methanol are added to the 4-non-1(E/Z)-enylmorpholine. The mixture is brought to 50° C. and 85.5 g (0.99 mol) of methyl acrylate are added over one hour. The mixture is stirred for fifteen hours at 50° C., and then a further 43.0 g (0.50 mol) of methyl acrylate are added over one hour thirty minutes. After the end of the addition, the mixture is stirred for a further twelve hours at 60° C. The temperature of the reaction medium is increased to 80° C. An aqueous solution of acetic acid buffered to pH 4 (195.7 g of acetic acid, 71.7 g of sodium acetate trihydrate and 232.6 g of water) are added dropwise over two hours at this temperature. Stirring is continued for a further four hours. The phases are allowed to settle and are separated. The aqueous phase is extracted twice with 150 ml of toluene. The organic phases are combined and are washed three times with 100 ml of water and once with 100 ml of brine. The resulting organic phase is dried over magnesium sulfate. After evaporating off the solvent under reduced pressure (3990 Pa), without exceeding 50° C. in the bulk, 237.0 g of crude oxo ester are obtained, and are blanched under high vacuum (70° C. to 120° C. at 93 Pa) to give 152.1 g of 91.0% methyl 4-formylundecanoate (yield: 0.61 mol; 61%).

EXAMPLE 4

Synthesis of 2-heptylpentane-1,5-diol (10)

390.0 g of isopropanol and 22.4 g (0.59 mol) of sodium borohydride are placed in a one-liter round-bottomed flask with a magnetic stirrer, a thermometer and an addition funnel. 148.4 g (0.59 mol) of 91% methyl 4-formylundecanoate (6) are added dropwise over one hour. The temperature in the bulk rises to 35° C. during the addition. The addition is continued for 29 hours, while allowing the temperature in the bulk to return to room temperature (about 20° C.). After cooling the reaction medium to 5° C., 8.6 g of acetone are added, without exceeding 10° C. in the bulk. The reaction medium is again cooled to 5° C. and 240.0 g of hydrochloric acid are added over one hour, without exceeding 10° C. in the bulk. 250.0 g of water are added to facilitate the separation of the phases. The aqueous phase is extracted twice with 200 ml of toluene. The organic phases are combined and are washed once with 100.0 ml of water and once with 100 ml of brine. The resulting organic phase is dried over magnesium sulfate and filtered. The solvent is evaporated off under reduced pressure (3990 Pa) without exceeding 50° C. in the bulk. 118.0 g (0.42 mol) of 72% 2-heptylpentane-1,5-diol (10) are obtained, and are used directly in the cyclization step.

EXAMPLE 5

Synthesis of 3-heptyltetrahydropyran (11)

60.6 g (0.21 mol) of 2-heptylpentane-1,5-diol are placed in a 500 ml round-bottomed flask with a magnetic stirrer, a condenser, a thermometer and an addition funnel, and 52.6 g of 85% phosphoric acid are rapidly added. The temperature in the reaction medium rises to 60° C. during the addition. The reaction mixture is brought to reflux (127° C.) and is stirred for four hours. The mixture is cooled to room temperature (about 20° C.) and 150 ml of water are added. Stirring is increased and continued for 30 minutes. The phases are separated and the aqueous phase is extracted once with 100 ml of methyl t-butyl ether. The organic phases are combined and are washed twice with 50 ml of saturated sodium bicarbonate solution and once with 50 ml of brine. The organic phase is dried and filtered, and the solvent is evaporated off under reduced pressure (3990 Pa), without exceeding 50° C. in the bulk. The crude product is then distilled on a Vigreux column. The core fraction contains 28.1 g (0.18 mol) of 96% 3-heptyltetrahydropyran (boiling point: 100° C. at 930 Pa). The yield is 73%.

The infrared, NMR and mass spectral analyses of the compounds obtained show that they correspond to the structures of the expected compounds.

EXAMPLE 6

Olfactory Evaluation

In a first stage, the fragrant characteristics of several pure compounds were evaluated by a panel. The evaluation panel is composed of several professionals, who qualitatively evaluate each compound. The compounds were described as fruity, lactonic with notes of fig or coriander leaves. The results of the evaluations are collated below:

- 5-propyltetrahydro-2H-pyran-2-one: lactonic, coconut, fig leaf, in the octahydrocoumarin register
- 5-pentyltetrahydro-2H-pyran-2-one: lactonic, lemony, green, verbena
- 3-heptyltetrahydropyran: lactonic, green, aldehyde, coriander leaf, mandarin, banana
- 3-benzyltetrahydropyran: geranium, woody, phenolic, lactonic.

5-Pentyltetrahydro-2H pyran-2-one and 5-heptyl-tetrahydro-2H-pyran-2-one were then tested in a nacreous shampoo base (compositions 1, 2 and 3, respectively). Their fragrant impact was assessed by comparing fragrancing compositions without and with each compound. 3-Benzyltetrahydropyran was tested in a nacreous shampoo base and in a concentrated softening base (compositions 4 and 5). Its fragrant impact was compared with that of styrallyl acetate.

Composition 1
Tiaré
(application 0.5% weight/weight of a nacreous shampoo base)

| Component | Test 1 (g) | Test 2 (g) |
|---|---|---|
| Benzyl acetate | 60.0 | 60.0 |
| Cinnamyl alcohol Synth. Prime[1] | 6.0 | 6.0 |
| Phenylethyl alcohol | 80.0 | 80.0 |
| Methyl anthranilate | 20.0 | 20.0 |
| Methyl benzoate | 2.0 | 2.0 |
| 98% citronellol | 60.0 | 60.0 |
| Coumarin | 4.0 | 4.0 |
| Pure geraniol | 56.0 | 56.0 |
| Methyl dihydrojasmonate | 200.0 | 200.0 |
| Crystalline heliotropin | 8.0 | 8.0 |
| Isoeugenol | 3.0 | 3.0 |
| Linalool | 100.0 | 100.0 |
| Lyral[2] | 130.0 | 130.0 |
| Methylionantheme | 40.0 | 40.0 |
| Benzyl salicylate | 200.0 | 200.0 |
| Folione[3] | 5.0 | 5.0 |
| 10% indole in DPG | 10.0 | 10.0 |
| 10% Methyl-para-cresol in DPG | 6.0 | 6.0 |
| Dipropylene glycol | 10.0 | 0.0 |
| 5-Pentyltetrahydro-2H-pyran-2-one | 0.0 | 10.0 |
| Total | 1000.0 | 1000.0 |

[1]Origin: Givaudan, Switzerland
[2]4-(4-Hydroxy-4-methylpentyl-3-cyclohexene-1-carbaldehyde; origin: International Flavors & Fragrances Inc., USA
[3]Methyl 2-octynoate, origin: Givaudan, Switzerland.

Composition 2
Lily of the valley
(application 0.5% by weight of a nacreous shampoo base)

| Component | Test 1 (g) | Test 2 (g) |
|---|---|---|
| Benzyl acetate | 56.0 | 56.0 |
| Phenylethyl alcohol | 445.0 | 445.0 |
| α-Hexylcinnamaldehyde | 100.0 | 100.0 |
| 98% Citronellol | 80.0 | 80.0 |
| Methyl dihydrojasmonate | 100.0 | 100.0 |
| Lilial[1] | 85.0 | 85.0 |
| Linalool | 110.0 | 110.0 |
| Triplal[2] | 1.0 | 1.0 |
| cis-3-Hexenol at 10% in DPG | 6.0 | 6.0 |
| Indole at 10% in DPG | 6.0 | 6.0 |
| Vanillin at 10% in DPG | 6.0 | 6.0 |
| Dipropylene glycol | 10.0 | 0.0 |
| 5-Heptyltetrahydro-2H-pyran-2-one | 0.0 | 10.0 |
| Total | 1000.0 | 1000.0 |

[1](2-Methyl-3(4-tert-butylphenyl)propanal, origin: Givaudan, Switzerland
[2]2,4-Dimethyl-3-cyclohexene-1-carbaldehyde, origin: International Flavors & Fragrances Inc., USA.

Composition 3
Peach
(application 0.5% by weight of a nacreous shampoo base)

| Component | Test 1 (g) | Test 2 (g) |
|---|---|---|
| Isoamyl acetate | 10.0 | 10.0 |
| Benzyl acetate | 65.0 | 65.0 |
| Phenylethyl alcohol | 40.0 | 40.0 |
| Allyl caproate | 5.0 | 5.0 |
| Givescone[1] | 5.0 | 5.0 |
| Methyl dihydrojasmonate | 145.0 | 145.0 |
| cis-3-Hexenol | 4.0 | 4.0 |
| α-ionone | 15.0 | 15.0 |
| cis-Jasmone[2] | 2.0 | 2.0 |
| Linalool | 175.0 | 175.0 |
| Neofolione[3] | 1.0 | 1.0 |
| Frambinone | 3.0 | 3.0 |
| γ-Nonalactone | 10.0 | 10.0 |
| Tetrahydrolinalool | 260.0 | 260.0 |
| Hexyl salicylate | 155.0 | 155.0 |
| Corps M020[4] | 80.0 | 80.0 |
| Ethyl butyrate at 10% in DPG | 5.0 | 5.0 |
| Dipropylene glycol | 20.0 | 0.0 |
| 5-Heptyltetrahydro-2H-pyran-2-one | 0.0 | 20.0 |
| Total | 1000.0 | 1000.0 |

[1]Ethyl-2-ethyl-6,6-dimethyl-2-cyclohexenecarboxylate and ethyl 2,3,6,6-tetramethyl-2-cyclohexenecarboxylate, origin: Givaudan, Switzerland.
[2]Origin: Givaudan, Switzerland
[3]Methyl 2-nonenoate, origin: Givaudan, Switzerland
[4]Specialty product of V. Mane Fils.

| Composition 4 Mulberry (application 0.5% by weight of a softening base) | | |
|---|---|---|
| Component | Test 1 (g) | Test 2 (g) |
| Blackcurrant MGO[(1)] | 30.0 | 30.0 |
| Isoamyl acetate | 6.0 | 6.0 |
| Benzyl acetate | 20.0 | 20.0 |
| Ethyl acetyl acetate | 25.0 | 25.0 |
| α-Hexylcinnamaldehyde | 55.0 | 55.0 |
| Lauryl aldehyde | 2.0 | 2.0 |
| Gamma-undecalactone 2 | 30.0 | 30.0 |
| | 45.0 | 45.0 |
| Bacdanol(2) | 10.0 | 10.0 |
| Thai benjoin at 50% in MEK | 2.0 | 2.0 |
| Butyl butyrate | 3.0 | 3.0 |
| Ethyl cinnamate | 4.0 | 4.0 |
| Lemon essence, Italy | 60.0 | 60.0 |
| Dipropylene glycol | 186.0 | 186.0 |
| cis-3-Hexenol | 5.0 | 5.0 |
| α-Ionone | 12.0 | 12.0 |
| β-Ionone | 18.0 | 18.0 |
| Lilial[(3)] | 30.0 | 30.0 |
| Distilled lime essence, Haiti | 20.0 | 20.0 |
| Linalool | 20.0 | 20.0 |
| Methylionantheme Super[(4)] | 35.0 | 35.0 |
| Musc T-ethylene brassylate[(5)] | 200.0 | 200.0 |
| Orange essence, Brazil | 30.0 | 30.0 |
| Frambinone[(6)] | 10.0 | 10.0 |
| Benzyl salicylate | 25.0 | 25.0 |
| Undecavertol[(7)] | 4.0 | 4.0 |
| Ethyl maltol - Veltol Plus[(8)] | 2.0 | 2.0 |
| Verdox[(9)] | 35.0 | 35.0 |
| Toluene-free benzaldehyde at 10% in DPG | 5.0 | 5.0 |
| cumin essence | 2.0 | 2.0 |
| Damascenones at 10% in DPG[(10)] | 7.0 | 7.0 |
| Folione at 10% in DPG[(11)] | 4.0 | 4.0 |
| Galbanum essence | 4.0 | 4.0 |
| Clove essence | 4.0 | 4.0 |
| Melonal at 10% in DPG[(12)] | 2.0 | 2.0 |
| 6-cis-Nonenol at 1% in DPG | 5.0 | 5.0 |
| Oxane at 10% in DPG[(13)] | 15.0 | 15.0 |
| Dimethyl sulfide at 1% in DPG | 15.0 | 15.0 |
| Styrallyl acetate | 25.0 | 0.0 |
| 3-Benzyltetrahydropyran | 0.0 | 25.0 |
| Total | 1000.0 | 1000.0 |

[(1)]Specialty product of V. Mane Fils
[(2)]2-Ethyl-4-(2,3,3-trimethyl-3-cyclopentyl-1-yl)-2-buten-1-ol, origin: International Flavors & Fragrances Inc. USA
[(3)]2-Methyl-3-(4-tert-butylphenyl)propanal, origin: Givaudan, Switzerland
[(4)]Origin: Givaudan, Switzerland
[(5)]1,4-Dioxacycloheptadecane-5,17-dione
[(6)]4-(4-Hydroxyphenyl)-2-butanone
[(7)]4-Methyl-3-decen-5-ol, origin: Givaudan, Switzerland
[(8)]2-Ethyl-3-hydroxypyran-4-one
[(9)]2-tert-Butylcyclohexan-1-ylacetate, origin: International Flavors & Fragrances Inc., USA.
[(10)]1-(2,6,6-Trimethyl-1,3-cyclohexadien-1-yl)-2-buten-1-one (isomers), origin: Firmenich, Switzerland
[(11)]Methyl 2-octynoate, origin: Givaudan, Switzerland
[(12)]2,6-Dimethyl-5-hepten-1-al, origin: Givaudan, Switzerland
[(13)]cis-2-Methyl-4-propyl-1,3-oxathiane, origin: Firmenich, Switzerland.

| Composition 5 Guava (application 0.5% by weight of a nacreous shampoo base and a softening base) | | |
|---|---|---|
| Component | Test 1 (g) | Test 2 (g) |
| Blackcurrant MGO[(1)] | 6.0 | 6.0 |
| cis-3-Hexenyl acetate VMF[(2)] | 70.0 | 70.0 |
| Dimethylbenzylcarbinyl acetate | 12.0 | 12.0 |
| Ethyl acetate | 6.0 | 6.0 |
| Hexyl acetate | 6.0 | 6.0 |
| Phenylethyl acetate | 10.0 | 10.0 |
| Ethyl acetyl acetate | 170.0 | 170.0 |
| Phenylethyl alcohol | 50.0 | 50.0 |
| γ-Undecalactone | 40.0 | 40.0 |
| cis-Isoambrettolide | 20.0 | 20.0 |
| Ethyl butyrate | 24.0 | 24.0 |
| Ethyl cinnamate | 140.0 | 140.0 |
| Dipropylene glycol | 124.0 | 124.0 |
| Rectified eugenol VMF[(2)] | 30.0 | 30.0 |
| γ-Decalactone | 30.0 | 30.0 |
| cis-3-Hexenol | 14.0 | 14.0 |
| cis-3-Hexenyl isobutyrate VMF[(2)] | 30.0 | 30.0 |
| β-Ionone | 12.0 | 12.0 |
| Musc T ethylene brassylate[(3)] | 30.0 | 30.0 |
| Orange terpenes Brazil | 20.0 | 20.0 |
| γ-Nonalactone | 10.0 | 10.0 |
| Tetrahydrolinalool | 50.0 | 50.0 |
| Vanillin | 14.0 | 14.0 |
| Grapefruit at 10% in DPG[(4)] | 6.0 | 6.0 |
| Methyl anthranilate at 10% in DPG | 8.0 | 8.0 |
| Ethylmaltol at 1% in DPG[(5)] | 20.0 | 20.0 |
| Corps M290 at 10% in DPG[(6)] | 8.0 | 8.0 |
| Styrallyl acetate | 8.0 | 0.0 |
| 3-Benzyltetrahydropyran | 0.0 | 8.0 |
| Total | 1000.0 | 1000.0 |

[(1)]Specialty product of V. Mane Fils
[(2)]Origin: V. Mane Fils
[(3)]1,4-Dioxacycloheptadecane-5,17-dione
[(4)]Specialty product of V. Mane Fils
[(5)]2-Ethyl-3-hydroxypyran-4-one
[(6)]Specialty product of V. Mane Fils In each case, the evaluations of the olfactory impact were conducted at $t_0$, $t_{+6h}$, $t_{+24h}$ to evaluate the head, core and back notes.

5-Pentyltetrahydro-2H-pyran-2-one gives composition 1 a lighter and more airy aspect.

5-Heptyltetrahydro-2H-pyran-2-one gives composition 2 a more transparent and green aspect. On the other hand, in composition 3, it gives a less green aspect, but a more fruit flesh aspect.

3-Benzyltetrahydropyran gives composition 4 a more natural rhubarb note with a green astringent woody aspect.

It gives composition 5 more volume and power by improving the guava note.

The loss of intensity over time appears to be quite linear, without revealing any major change in fragrant nature.

The results of these evaluations show without the slightest doubt that the compounds described above have advantageous olfactory characteristics, which will find an application in particular in cosmetics, perfumery, maintenance products and, in general, in any fragrant composition in which it is desired to mask or neutralize odor.

The invention claimed is:

1. A perfumery composition comprising at least one compound selected from the group consisting of:
   5-pentyltetrahydropyran-2-one and
   5-heptyltetrahydropyran-2-one,
   wherein said at least one compound is mixed with a composition selected from the group consisting of fragrancing bases, fragrancing concentrates, eaux de Cologne, and eaux de toilette fragrance.

2. A perfumery composition comprising at least one compound selected from the group consisting of:
- 5-pentyltetrahydropyran-2-one and
- 5-heptyltetrahydropyran-2-one,
  wherein said perfumery composition is selected from the group consisting of topical compositions, cosmetic compositions, facial cream, body cream, talc powder, hair oil, shampoo, hair lotions, bath salts and oils, shower and bath gel, toiletry soap, antiperspirant, body deodorant, shaving lotion shaving cream, soap, cream, toothpaste, mouthwash, and salves.

3. A perfumery composition comprising at least one compound selected from the group consisting of:
- 5-pentyltetrahydropyran-2-one and
- 5-heptyltetrahydropyran-2-one,
  wherein said perfumery composition is selected from the group consisting of a maintenance product, softener, detergent, laundry washing product and ambient deodorizer.

4. The perfumery composition of claim 1, wherein said compound is 5-pentyltetrahydropyran-2-one.

5. A perfumery composition comprising at least one compound selected in the group consisting of:
- 3-benzyl-tetrahydropyran and
- 3-heptyl-tetrahydropyran,
  wherein said at least one compound is mixed with a composition selected from the group consisting of fragrancing bases, fragrancing concentrates, eaux de Cologne, and eaux de toilette fragrance.

6. The perfumery composition of claim 5, wherein said compound is 3-benzyl-tetrahydropyran.

7. The perfumery composition of claim 5, wherein said compound is 3-heptyl-tetrahydropyran.

8. A perfumery composition comprising at least one compound selected in the group consisting of:
- 3-benzyl-tetrahydropyran and
- 3-heptyl-tetrahydropyran,
  wherein said perfumery composition is selected from the group consisting of topical compositions, cosmetic compositions, facial cream, body cream, talc powder, hair oil, shampoo, hair lotions, bath salts, shower and bath gel, toiletry soap, antiperspirant, body deodorant, shaving lotion shaving cream, soap, cream, toothpaste, mouthwash and salves.

9. A perfumery composition comprising at least one compound selected in the group consisting of:
- 3-benzyl-tetrahydropyran and
- 3-heptyl-tetrahydropyran,
  wherein said perfumery composition is selected from the group consisting of a softener, detergent, laundry washing product and ambient deodorizer.

10. The perfumery composition of claim 2, wherein said compound is 5-pentyltetrahydropyran-2-one.

11. The perfumery composition of claim 3, wherein said compound is 5-pentyltetrahydropyran-2-one.

12. The perfumery composition of claim 8, wherein said compound is 3-benzyl-tetrahydropyran.

13. The perfumery composition of claim 8, wherein said compound is 3-heptyl-tetrahydropyran.

14. The perfumery composition of claim 9, wherein said compound is 3-benzyl-tetrahydropyran.

15. The perfumery composition of claim 9, wherein said compound is 3-heptyl-tetrahydropyran.

* * * * *

UNITED STATES PATENT AND TRADEMARK OFFICE
CERTIFICATE OF CORRECTION

PATENT NO.         : 8,440,608 B2
APPLICATION NO.    : 11/659501
DATED              : May 14, 2013
INVENTOR(S)        : Jean Mane et al.

Page 1 of 1

It is certified that error appears in the above-identified patent and that said Letters Patent is hereby corrected as shown below:

On the title page, Item (54) and in the specification, column 1, the title to read as follows:

-- BETA-SUBSTITUTED TETRAHYDROPYRAN(ONE)S AND METHOD FOR THE SYNTHESIS AND THE USE THEREOF --

Signed and Sealed this
Twenty-second Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,440,608 B2  Page 1 of 1
APPLICATION NO. : 11/659501
DATED : May 14, 2013
INVENTOR(S) : Mane et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 441 days.

Signed and Sealed this
Eighth Day of September, 2015

Michelle K. Lee
*Director of the United States Patent and Trademark Office*